United States Patent [19]

Whitehurst et al.

[11] 4,444,794

[45] Apr. 24, 1984

[54] PRODUCTION OF ALKALI METAL GLUCOHEPTANATE FROM SWEET POTATOES

[76] Inventors: Brooks M. Whitehurst, 1983 Hoods Creek Dr., New Bern, N.C. 28560; Donald F. Clemens, 1701 Sulgrave Rd., Greenville, N.C. 27834

[21] Appl. No.: 386,353

[22] Filed: Jun. 8, 1982

[51] Int. Cl.³ .................... A23K 1/14; C12P 19/02; C12P 19/14; C12P 19/02
[52] U.S. Cl. ..................... 426/52; 426/53; 435/96; 435/99; 435/105
[58] Field of Search .............. 426/49, 52, 53, 271, 426/637, 7; 435/99, 96, 105

[56] References Cited

U.S. PATENT DOCUMENTS

| | | | |
|---|---|---|---|
| 3,022,343 | 2/1962 | Behnke | 260/528 |
| 3,169,876 | 2/1965 | Hoover | 99/207 |
| 3,407,074 | 10/1968 | Hoover | 99/100 |
| 3,922,200 | 11/1975 | Walon et al. | 435/96 |
| 4,361,651 | 11/1982 | Keim | 435/96 |

*Primary Examiner*—David M. Naff
*Assistant Examiner*—Marianne S. Minnick
*Attorney, Agent, or Firm*—John S. Roberts, Jr.

[57] ABSTRACT

Alkali metal glucoheptonate is produced from sweet potatoes by reducing the size of sweet potatoes to particles of about 1/16 inch, slurrying the sweet potato particles, adding a-amylase to the slurry, boiling the slurry and filtering to separate a liquid syrup and a protein-containing pulp residue, cooling the liquid syrup and adding glucoamylase, boiling the resulting liquid syrup, and adding an alkali metal cyanide to the liquid syrup and heating to produce the alkali metal glucoheptanate. The alkali metal glucoheptanate is suitable for use as a water conditioning chelant and the protein-containing pulp residue is suitable for use as animal food.

1 Claim, No Drawings

PRODUCTION OF ALKALI METAL GLUCOHEPTANATE FROM SWEET POTATOES

This invention relates to processes and commercial products obtained from sweet potatoes.

PRIOR ART

U.S. Pat. No. 3,022,343 (Behnke) teaches a method of producing sodium glucoheptanate, from corn syrup.

U.S. Pat. No. 3,033,900 (Holstein) teaches a process for the production of a pure grade of calcium glucoheptanate, using sodium glucoheptanate as a starting material.

U.S. Pat. No. 3,407,074 (Hoover) teaches a process for saccharifying and liquefying sweet potatoes using a flash heating process.

U.S. Pat. No. 3,169,876 (Hoover) teaches a process for producing dehydrated sweet potato from sweet potato puree using only $\alpha$ or $\beta$ amylase enzyme.

UTILITY

This invention teaches the convertion of sweet potatoes into by-products with economic value. Starch from the sweet potato is converted into monosaccharides which, in turn, are converted into a chelant useful as a water-conditioner; the protein residue is an economical cereal-like food for humans and animals.

GENERAL DESCRIPTION

Sweet potatoes are a substantial crop in the southeastern United States. The industry, however, wastes an estimated 100–150 bushels per acre of sweet potatoes because canneries accept only a specific size sweet potato. To date, little use has been made of the jumbos and the culls, the sweet potatoes rejected because they are too large or too small.

The sweet potato plant, an annual vine related to the morning glory, produces a fleshy root whose high energy value is exceeded only by dried beans and peas. The root contains significant amounts of vitamins A and C and is rich in starch and proteins. World production exceeds 130,000,000 tons annually.

Time cooking process alone is well-known in the art and amounts to harvesting the root, peeling and trimming excess parts, and then boiling the root in water. The teachings of this invention amplify this simple process by separating the starch and protein constituents, converting the starch into a chelant and drying the protein into a food product suitable for animal and human consumption.

In the production of saccharides from the starch component of sweet potatoes, the enzyme, $\alpha$-amylase, may be added to the cooking step. This is a necessary ingredient to be used if the sweet potatoes have been stored (as opposed to newly harvested). This enzyme reduces the polymer size of the starch molecule to facilitate the starch conversion to monosaccharides and to limit dextrins, a mixture which ranges from di- to about hexasaccharides. Gluco-amylase is then added. This enzyme converts the polysaccharides into glucose. Again, the inclusion of $\alpha$-amylase is required only if the sweet potatoes have been stored for longer than seven days. The chart below shows that fresh sweet potatoes (those stored for less than seven days) are not significantly affected by the addition of $\alpha$-amylase.

| Freshly Harvested | No $\alpha$-amylase Gal Ethanol/100 wt. | 0.05% $\alpha$-amylase Gal Ethanol/100 wt. |
|---|---|---|
| Centennial | 1.16 | 1.23 |
| Porto Rico | 1.34 | 1.41 |
| Jewel | 1.04 | 1.07 |
| 10 Months Old | | |
| Porto Rico | 0.19 | 1.07 |

SPECIFIC DESCRIPTION

A process and resulting products for the utilization of products from sweet potatoes comprising separating a sweet potato slurry into carbohydrate and protein. The carbohydrate portion is converted into a chelant via a Kiliani-Fischer reaction. The protein component is dried and used as proteinconcentrate in animal and human food products. In the process, fresh sweet potatoes (up to and including seven days old) are preferred.

The sweet potato cooking process separates a sweet potato into liquid syrup consisting primarily of stach and a fibrous vegetable-like product consisting of protein, carotene, and fiber. The starch component, which can be converted to monosaccharides, is used in the synthesis of sodium glucoheptanate, an effective chelant. The fibrous product, a high protein concentrate, is dried and used as human and animal food products. Sweet potatoes were chopped to about 1/16 inch size and slurried in tap water. The particle size of the chopped sweet potato is critical to the separation of the syrup from the pulp. If the pulp size is very fine, such as a puree, the separation of the syrup from the pulp is very difficult. If the pulp particle size is too large, removal of the carbohydrate from the sweet potato will be substantially reduced. If the potatoes had been stored, $\alpha$-amylase enzyme is added and the pulp slurry boiled for approximately 30 minutes. The pulp slurry is then filtered, the solution cooled to room temperature, and gluco-amylase enzyme added. At this point the solution should stand to allow the enzyme to work, then the solution is boiled in order to produce a syrup with a density range from 1.14 g/ml to 1.35 g/ml.

From this point the teaching of this invention splits into two parts: (1) adding sodium cyanide to the syrup produces a chelant; and (2) drying the pulp residue yields a protein concentrate useful for conversion into human and animal foods.

Time Chelant: The newly harvested potato contains high levels of starch. This starch is converted into monosaccharides by the addition of gluco-amylase, as detailed earlier. The subsequent addition of an effective amount of sodium cyanide produces a chelant. This process is known as the Kiliani-Fischer synthesis reaction:

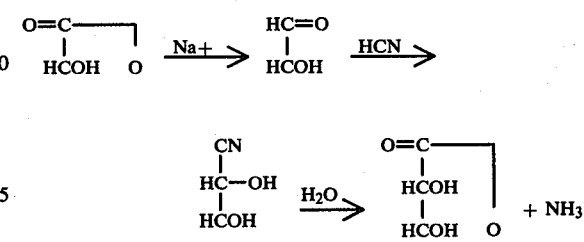

The teaching of this invention prefers the addition of 0.05 to 0.07 g NaCN per gram of sweet potato syrup. Chemically, a cyanide group is added to the aldehyde portion of glucose. This results in the addition of a carbon aom to a 6-carbon chain. Subsequent heating produces the chelant sodium glucoheptanate plus a by-product of ammonia. The effectiveness of this chelant is shown in the examples.

The second use of sweet potato products utilizes the pulp residue after the liquid syrup is decanted from the pulp slurry. This residue is a high protein vegetable-like product consisting primarily of protein, carotene, and fiber. The product remaining after drying the residue is a source of protein for animals (as illustrated in Example 4). The protein level of the dried residue is approximately 30%.

EXAMPLE 1

Process for the Production of a Water Conditioning Chelate from Sweet Potatoes.

3686 g of white Hayman sweet potatoes were chopped in a food mill to about 1/16 inch in size. The chopped sweet potato was mixed with 3600 ml of tap water and 2 teaspoons of the enzyme alpha amylase. The pulp slurry was boiled for 30 minutes, and while at the boiling temperature was filtered through a large Buchner funnel. About 4000 ml of solution was collected with a specific gravity of 1.068. After cooling to room temperature, ½ teaspoon of gluco-amylase enzyme was added to the solution. After 1 hr. of standing, the solution was then brought to a boil unit 1200 ml of syrup was remaining. The density of the syrup at room temperature was 1.168 g/ml.

To 500 g of this syrup, 27.8 g of NaCN was added and the mixture warmed to 76° C. Considerable ammonia was evolved. This solution was analyzed for its chelating power. Using a standard test, the solution would chelate 173 mg of $Ca^{++}$ per g of chelant and 670 mg of $Fe^{+++}$ per g of chelant.

EXAMPLE 2

To test the effectiveness of the chelant, an independent agency determined the chelating ability of the product:

| | Product Density | Mg of Calcium per Gram Chelant | Mg of Iron per Gram Chelant |
|---|---|---|---|
| Sample 159-a | 1.165 g/l | 152.1 | 425.0 |
| Sample 159-2 | 1.274 g/l | 239.5 | 750.0 |

EXAMPLE 3

The production of alcohol from sweet potatoes has been shown to be a function of variety, percent dry matter, and yield per acre. Using the process detailed in the specific description of the invention, the alcohol yield is shown below.

| Variety | Dry Matter (%) | Alcohol Yield, Gal. Anhydrous (Freshly Dug) | Total Potato Yield CWT/A | Alcohol Yield Gal/A |
|---|---|---|---|---|
| Porto Rico, Red | 26.2 | 1.41 gal/CWT | — | — |
| Jewel, Yellow | 23.8 | 1.07 | 297 | 318 |
| Centennial, Yellow | 25.9 | 1.23 | 365 | 450 |
| Pelican Processor, White | 26.7 | 1.54 | — | — |
| Rojo Blanco, White | 24.9 | 1.40 | 254 | 355 |
| Whitestar, White | 26.4 | 1.48 | — | — |
| Vogel, White | 28.2 | 1.65 | — | — |

| | Yield (Bu/A) | Starch in Roots (%) | Starch (Lb/A) | Fermentable Carbo hydrates | Theoretical Alcohol Yield (Gal/A) |
|---|---|---|---|---|---|
| Southern Queen | 416 | 19.07 | 4443 | 22.76 | 474 |
| Brazilian | 450 | 16.46 | 4118 | 20.57 | 462 |
| Vineland Bunch Yam | 141 | 19.22 | 1483 | 22.28 | 168 |
| Arkansas Beauty | 158 | 14.43 | 1277 | 18.64 | 153 |
| Corn | 100 | — | — | — | 250 |

EXAMPLE 4

On Farm System: On a farm in Wilson, N.C., the farmer followed this procedure: Twenty bushels of sweet potatoes, approximately 1000 pounds, were placed in a wood fired open top cooker with approximately 875 pounds of water. This mixture was then cooked and converted according to the processes herein detailed. The farmer uses this system to produce 180 proof ethanol capable of driving his farm vehicles and feeds the pulp residue to his livestock.

We claim:

1. A method for production from sweet potatoes of an alkali metal glucoheptonate chelant suitable for use as a water conditioning chelant which comprises
   (a) Harvesting sweet potatoes, reducing the sweet potatoes to particles of about 1/16 inch in size, slurrying the sweet potato particles to produce an acqueous slurry and adding α-amylase to the slurry to reduce the polymer size of starch molecules contained by the sweet potatoes;
   (b) Boiling the slurry from step (a) and filtering the boiled slurry to separate a liquid syrup, and a protein-containing pulp residue suitable for animal food;
   (c) Cooling the liquid syrup from step (b) and adding glucoamylase to convert polysaccharides in the liquid syrup to glucose;
   (d) Boiling the liquid syrup containing glucose from step (c) for a time sufficient to obtain a liquid syrup having a density of about 1.14 g/ml to about 1.35 g/ml;
   (e) Adding an alkali metal cyanide to the liquid syrup from step (d) and heating to produce an alkali metal glucoheptanate chelant.

* * * * *